US009886939B2

(12) United States Patent
Griffin

(10) Patent No.: US 9,886,939 B2
(45) Date of Patent: Feb. 6, 2018

(54) SYSTEMS AND METHODS FOR ENHANCING A SIGNAL-TO-NOISE RATIO

(71) Applicant: Signal/Noise Solutions L.L.C., San Marcos, TX (US)

(72) Inventor: Remington Griffin, San Marcos, TX (US)

(73) Assignee: Signal/Noise Solutions, L.L.C., San Marcos, TX (US)

( * ) Notice: Subject to any disclaimer, the term of this patent is extended or adjusted under 35 U.S.C. 154(b) by 0 days.

(21) Appl. No.: 15/628,610

(22) Filed: Jun. 20, 2017

(65) Prior Publication Data

US 2017/0309268 A1 Oct. 26, 2017

(51) Int. Cl.

| | |
|---|---|
| ***H03G 3/00*** | (2006.01) |
| ***G10K 11/178*** | (2006.01) |
| ***H04R 3/04*** | (2006.01) |
| *A61F 11/06* | (2006.01) |

(52) U.S. Cl.

CPC .......... *G10K 11/1782* (2013.01); *H04R 3/04* (2013.01); *G10K 2210/1053* (2013.01); *G10K 2210/1081* (2013.01); *G10K 2210/116* (2013.01); *G10K 2210/1281* (2013.01); *G10K 2210/3044* (2013.01); *G10K 2210/3056* (2013.01)

(58) Field of Classification Search

CPC ....... G10K 11/1782; G10K 2210/1053; G10K 2210/1081; G10K 2210/116; G10K 2210/1281; G10K 2210/3044; G10K 2210/3056; H04R 3/04

USPC .................................................. 381/63, 71.1

See application file for complete search history.

(56) References Cited

U.S. PATENT DOCUMENTS

| | | | | |
|---|---|---|---|---|
| 3,631,365 | A | 12/1971 | Dolby | |
| 3,989,897 | A | 11/1976 | Carver | |
| 4,218,585 | A | 8/1980 | Carver | |
| 4,309,570 | A | 1/1982 | Carver | |
| 4,815,141 | A | 3/1989 | Carver et al. | |
| 2016/0255453 | A1* | 9/2016 | Fueg | G10L 19/008 381/1 |

OTHER PUBLICATIONS

Acoustic resonance, Wikipedia, Jun. 9, 2017, https://en.wikipedia.org/wiki/Acoustic_resonance.

Sympathetic resonance, Wikipedia, Aug. 17, 2016, https://en.wikipedia.org/wiki/Sympathetic_resonance.

* cited by examiner

*Primary Examiner* — Vivian Chin

*Assistant Examiner* — Ammar Hamid

(74) *Attorney, Agent, or Firm* — James J. Pohl; FisherBroyles, LLP

(57) ABSTRACT

Provided are methods and apparatus for enhancing a signal-to-noise ratio. In an example, provided is an apparatus configured to modify audio to better match the way the human brain processes audio by modifying the audio to a form which takes advantage of human echolocation capabilities. When humans listen to audio, they subconsciously listen for an echo and thus subconsciously focus on listening to, and for, meaningful information in audio. The focus causes humans to ignore noise in the audio, which results in enhancing a signal-to-noise ratio.

30 Claims, 9 Drawing Sheets

500

505

SYSTEMS AND METHODS FOR ENHANCING A SIGNAL-TO-NOISE RATIO

FIELD OF DISCLOSURE

This disclosure relates generally to the technical field of electronics, and more specifically, but not exclusively, to methods and apparatus which enhance a signal-to-noise ratio.

BACKGROUND

Audio in an electronic form can include noise. To a human listener, noise in audio can sound like "hissing," "wooshing," or unintelligible crowd noise. Many different mechanisms cause noise in audio, including random Gaussian noise generated by electrical components processing audio, air blowing on a microphone, a microphone or hydrophone detecting movement of fluids such as rain or waves, cosmic background radiation affecting electrical components processing audio, solar radiation affecting electrical components processing audio, electrical storms affecting electrical components processing audio, a vibrating machine (e.g., a fan) near a microphone, and crowds of people talking near a microphone (such as in a restaurant, club, conference hall, concert hall, etc.). Noise is a problem because it interferes with listening to meaningful information in audio. Meaningful information in audio includes speech, music, and other informative sounds. Noise is distracting and can induce a human listener to lose focus on listening to meaningful information in audio.

Conventional methods and apparatus, such as audio recording devices, audio processing devices, audio transmission devices, audio amplifying devices, and audio reproduction devices are not sufficiently equipped to mitigate effects of noise. Accordingly, there are previously unaddressed and long-felt industry needs for methods and apparatus which improve upon conventional methods and apparatus.

SUMMARY

This summary provides a basic understanding of some aspects of the present teachings. This summary is not exhaustive in detail, and is neither intended to identify all critical features, nor intended to limit the scope of the claims.

Example methods and apparatus for enhancing a signal-to-noise ratio are provided. In an example, provided is a first apparatus configured to enhance a signal-to-noise ratio. The first apparatus includes a physical processor and a memory communicably coupled to the physical processor. The memory stores instructions configured to cause the physical processor to initiate generating a noise-cancelled digital audio stream from an input digital audio stream. The generating the noise-cancelled digital audio stream includes identifying a noise portion of the input digital audio stream, inverting the identified noise portion, and adding the inverted identified noise portion to the input digital audio stream. The memory also stores instructions configured to cause the physical processor to initiate generating, using at least one intermediate delay reverberator, at least one respective intermediate delay reverberator output from the input digital audio stream. The memory also stores instructions configured to cause the physical processor to initiate generating, using at least one maximum delay reverberator, at least one respective maximum delay reverberator output from the input digital audio stream. Further, the memory stores instructions configured to cause the physical processor to initiate combining the noise-cancelled digital audio stream, the at least one respective intermediate delay reverberator output, and the at least one respective maximum delay reverberator output to form an output digital audio stream having the enhanced signal-to-noise ratio. In an example, the memory further stores instructions configured to cause the processor to initiate normalizing an intensity of the output digital audio stream to substantially an intensity of the input digital audio stream by weighting at least one of the noise-cancelled digital audio stream, the at least one respective intermediate delay reverberator output, or the at least one respective maximum delay reverberator output. In another example, the generating at least one respective intermediate delay reverberator output includes weighting the input digital audio stream with a respective wet weight to produce a respective wet-weighted digital audio stream, reverberating the respective wet-weighted digital audio stream with the at least one intermediate delay reverberator to create at least one respective intervening output, weighting the input digital audio stream with a respective dry weight to produce a respective dry-weighted digital audio stream, and producing the at least one respective intermediate delay reverberator output by combining the at least one respective intervening output with the respective dry-weighted digital audio stream. A ratio of the respective dry weight to the respective wet weight can be in an inclusive range between one-to-one and twenty-to-one. In a further example, the generating at least one respective maximum delay reverberator output includes weighting the input digital audio stream with a respective wet weight to produce a respective wet-weighted digital audio stream, reverberating the respective wet-weighted digital audio stream with the at least one maximum delay reverberator to create at least one respective intervening output, weighting the input digital audio stream with a respective dry weight to produce a respective dry-weighted digital audio stream, and producing the at least one respective maximum delay reverberator output by combining the at least one respective intervening output with the respective dry-weighted digital audio stream. In this further example, a ratio of the respective dry weight to the respective wet weight can be in an inclusive range between one-to-one and twenty-to-one. In another example, the generating at least one respective maximum delay reverberator output includes delaying the input digital audio stream by a maximum delay in an inclusive range between one sample cycle to thirty sample cycles of the input digital audio stream. In an example, the memory further stores instructions configured to cause the processor to at least one of: initiate attenuating, prior to initiating the combining, the at least one respective intermediate delay reverberator output; or initiate attenuating, prior to initiating the combining, the at least one respective maximum delay reverberator output. In an example, the physical processor is at least one of a microprocessor, a microcontroller, a digital signal processor, a field programmable gate array, a programmable logic device, an application-specific integrated circuit, a controller, a non-generic special-purpose processor, a state machine, a gated logic device, a discrete hardware component, or a dedicated hardware finite state machine, or a combination thereof. In an example, the first apparatus can be a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft. In an example, one or more parts of the first apparatus can be communicatively coupled to a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft. In an example, one or more portions of the first apparatus can be integrated in a semiconductor device, with the semiconductor device optionally being integrated in a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft.

In another example, a method for enhancing a signal-to-noise ratio is provided. The method includes generating a noise-cancelled digital audio stream from an input digital audio stream by identifying a noise portion of the input digital audio stream, inverting the identified noise portion, and adding the inverted identified noise portion to the input digital audio stream. The method also includes generating, using at least one intermediate delay reverberator, at least one respective intermediate delay reverberator output from the input digital audio stream. The method further includes generating, using at least one maximum delay reverberator, at least one respective maximum delay reverberator output from the input digital audio stream. The method also includes combining the noise-cancelled digital audio stream, the at least one respective intermediate delay reverberator output, and the at least one respective maximum delay reverberator output to form an output digital audio stream having the enhanced signal-to-noise ratio. In an example, the method includes normalizing an intensity of the output digital audio stream to substantially an intensity of the input digital audio stream by weighting at least one of the noise-cancelled digital audio stream, the at least one respective intermediate delay reverberator output, or the at least one respective maximum delay reverberator output. In an example, the generating at least one respective intermediate delay reverberator output includes weighting the input digital audio stream with a respective wet weight to produce a respective wet-weighted digital audio stream, reverberating the respective wet-weighted digital audio stream with the at least one intermediate delay reverberator to create at least one respective intervening output, weighting the input digital audio stream with a respective dry weight to produce a respective dry-weighted digital audio stream, and producing the at least one respective intermediate delay reverberator output by combining the at least one respective intervening output with the respective dry-weighted digital audio stream. In this example, a ratio of the respective dry weight to the respective wet weight can be in an inclusive range between one-to-one and twenty-to-one. In a further example, the generating at least one respective maximum delay reverberator output includes weighting the input digital audio stream with a respective wet weight to produce a respective wet-weighted digital audio stream, reverberating the respective wet-weighted digital audio stream with the at least one maximum delay reverberator to create at least one respective intervening output, weighting the input digital audio stream with a respective dry weight to produce a respective dry-weighted digital audio stream, and producing the at least one respective maximum delay reverberator output by combining the at least one respective intervening output with the respective dry-weighted digital audio stream. In this further example, a ratio of the respective dry weight to the respective wet weight can be in an inclusive range between one-to-one and twenty-to-one. In another example, the generating at least one respective maximum delay reverberator output includes delaying the input digital audio stream by a maximum delay in an inclusive range between one sample cycle to thirty sample cycles of the input digital audio stream. In an example, the method further includes at least one of: attenuating, prior to the combining, the at least one respective intermediate delay reverberator output; or attenuating, prior to the combining, the at least one respective maximum delay reverberator output.

In another example, provided is a non-transitory computer-readable medium, comprising processor-executable instructions stored thereon. The processor-executable instructions are configured to cause a processor to initiate generating a noise-cancelled digital audio stream from an input digital audio stream. The generating the noise-cancelled digital audio stream includes identifying a noise portion of the input digital audio stream, inverting the identified noise portion, and adding the inverted identified noise portion to the input digital audio stream. The processor-executable instructions are also configured to cause the processor to initiate generating, using at least one intermediate delay reverberator, at least one respective intermediate delay reverberator output from the input digital audio stream. The processor-executable instructions are also configured to cause the processor to initiate generating, using at least one maximum delay reverberator, at least one respective maximum delay reverberator output from the input digital audio stream. Further, the processor-executable instructions are also configured to cause the processor to initiate combining the noise-cancelled digital audio stream, the at least one respective intermediate delay reverberator output, and the at least one respective maximum delay reverberator output to form an output digital audio stream having the enhanced signal-to-noise ratio. In an example, the processor-executable instructions further include instructions configured to cause the processor to initiate normalizing an intensity of the output digital audio stream to substantially an intensity of the input digital audio stream by weighting at least one of the noise-cancelled digital audio stream, the at least one respective intermediate delay reverberator output, or the at least one respective maximum delay reverberator output. In another example, the generating at least one respective intermediate delay reverberator output includes weighting the input digital audio stream with a respective wet weight to produce a respective wet-weighted digital audio stream, reverberating the respective wet-weighted digital audio stream with the at least one intermediate delay reverberator to create at least one respective intervening output, weighting the input digital audio stream with a respective dry weight to produce a respective dry-weighted digital audio stream, and producing the at least one respective intermediate delay reverberator output by combining the at least one respective intervening output with the respective dry-weighted digital audio stream. A ratio of the respective dry weight to the respective wet weight can be in an inclusive range between one-to-one and twenty-to-one. In a further example, the generating at least one respective maximum delay reverberator output includes weighting the input digital audio stream with a respective wet weight to produce a respective wet-weighted digital audio stream, reverberating the respective wet-weighted digital audio stream with the at least one maximum delay reverberator to create at least one respective intervening output, weighting the input digital audio stream with a respective dry weight to produce a respective dry-weighted digital audio stream, and producing the at least one respective maximum delay reverberator output by combining the at least one respective intervening output with the respective dry-weighted digital audio stream. In this further example, a ratio of the respective dry weight to the respective wet weight can be in an inclusive range between one-to-one and twenty-to-one. In another example, the generating at least one respective maximum delay reverberator output includes delaying the input digital audio stream by a maximum delay in an inclusive range between one sample cycle to thirty sample cycles of the input digital audio stream. In another example, the processor-executable instructions further include instructions configured to cause the processor to at least one of: initiate attenuating, prior to the combining, the at least one respective intermediate delay reverberator output; or initiate attenuating, prior to the combining, the at least one respective maximum delay reverberator output. The non-transitory computer-readable medium, the processor, or both can be integrated with a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft.

In another example, provided is a second apparatus configured to enhance a signal-to-noise ratio. The second apparatus includes means for generating a noise-cancelled digital audio stream from an input digital audio stream. The means for generating the noise-cancelled digital audio stream includes means for identifying a noise portion of the input digital audio stream, means for inverting the identified noise portion, and means for adding the inverted identified noise portion to the input digital audio stream. The second apparatus also includes means for generating at least one respective intermediate delay output from the input digital audio stream. The second apparatus also includes means for generating at least one respective maximum delay output from the input digital audio stream. The second apparatus also includes means for combining the noise-cancelled digital audio stream, the at least one respective intermediate delay output, and the at least one respective maximum delay output to form an output digital audio stream having the enhanced signal-to-noise ratio. In an example, the second apparatus includes means for normalizing an intensity of the output digital audio stream to substantially an intensity of the input digital audio stream by weighting at least one of the noise-cancelled digital audio stream, the at least one respective intermediate delay output, or the at least one respective maximum delay output. In an example, the means for generating at least one respective intermediate delay output include means for weighting the input digital audio stream with a respective wet weight to produce a respective wet-weighted digital audio stream, means for delaying the respective wet-weighted digital audio stream to create at least one respective intervening output, means for weighting the input digital audio stream with a respective dry weight to produce a respective dry-weighted digital audio stream, and means for producing the at least one respective intermediate delay output by combining the at least one respective intervening output with the respective dry-weighted digital audio stream. A ratio of the respective dry weight to the respective wet weight can be in an inclusive range between one-to-one and twenty-to-one. In a further example, the means for generating at least one respective maximum delay output include means for weighting the input digital audio stream with a respective wet weight to produce a respective wet-weighted digital audio stream, means for delaying the respective wet-weighted digital audio stream to create at least one respective intervening output, means for weighting the input digital audio stream with a respective dry weight to produce a respective dry-weighted digital audio stream, and means for producing the at least one respective maximum delay output by combining the at least one respective intervening output with the respective dry-weighted digital audio stream. In this further example, a ratio of the respective dry weight to the respective wet weight can be in an inclusive range between one-to-one and twenty-to-one. In another example, the means for generating at least one respective maximum delay output includes means for delaying the input digital audio stream by a maximum delay in an inclusive range between one sample cycle to thirty sample cycles of the input digital audio stream. In an example, the second apparatus includes at least one of: means for attenuating, prior to the combining, the at least one respective intermediate delay output; or means for attenuating, prior to the combining, the at least one respective maximum delay output. The second apparatus can include a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft, of which the means for generating at least one respective intermediate delay output is a constituent part. In an example, one or more parts of the second apparatus can be integrated with a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft. In an example, one or more parts of the second apparatus can be integrated in a semiconductor device, with the semiconductor device optionally being integrated in a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft.

The foregoing broadly outlines some of the features and technical advantages of the present teachings so the detailed description and drawings can be better understood. Additional features and advantages are also described in the detailed description. The conception and disclosed examples can be used as a basis for modifying or designing other devices for carrying out the same purposes of the present teachings. Such equivalent constructions do not depart from the technology of the teachings as set forth in the claims. The inventive features characteristic of the teachings, together with further objects and advantages, are better understood from the detailed description and the accompanying drawings. Each of the drawings is provided for the purpose of illustration and description only, and does not limit the present teachings.

BRIEF DESCRIPTION OF THE DRAWINGS

The accompanying drawings are presented to describe examples of the present teachings, and are not limiting.

Figure 1A:
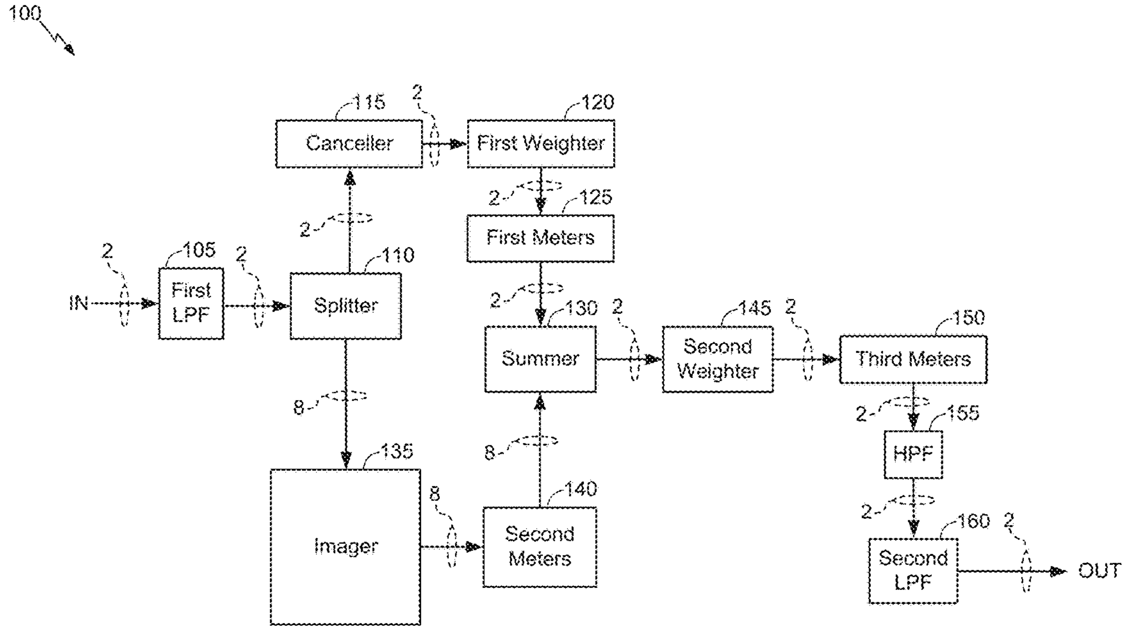
FIGS. 1A-1B depicts an example audio processing apparatus configured to enhance a signal-to-noise ratio.

In accordance with common practice, the features depicted by the drawings may not be drawn to scale. Accordingly, the dimensions of the depicted features may be arbitrarily expanded or reduced for clarity. In accordance with common practice, some of the drawings are simplified for clarity. Thus, the drawings may not depict all components of a particular apparatus or method. Further, like reference numerals denote like features throughout the specification and figures.

DETAILED DESCRIPTION

Provided are methods and apparatuses which enhance a signal-to-noise ratio. In an example, provided is an apparatus configured to modify audio to better match the way the human brain processes the audio by modifying the audio to a form which takes advantage of human echolocation capabilities. In an example, the apparatus adds, to the audio, at least one echo of the audio.

As humans evolved, they developed echolocation to detect direction and distance of objects, food, and threats. Even today, humans are born with echolocation abilities. Humans perform echolocation by sensing at least one echo of a sound, such as from the sound being reflected from an object, a wall, the like, or a combination thereof. Thus, when humans listen to audio, they subconsciously listen for an echo and thus subconsciously focus on listening to, and for, meaningful echo information in the audio. This focus causes humans to ignore noise in the audio, which results in enhancing a signal-to-noise ratio.

The examples disclosed hereby advantageously address the long-felt industry needs, as well as other previously unidentified needs, and mitigate shortcomings of conventional techniques. Among other advantages, an advantage provided by the examples is an improvement in signal-to-noise ratio over conventional devices. The systems and methods described herein can improve the functioning of devices configured to process audio, improve the performance of devices configured to process audio, or both. Moreover, the systems and methods described herein can improve the functioning of devices configured to reproduce audio, improve the performance of devices configured to reproduce audio, or both. The disclosed systems and methods can also improve the fields of audio processing and audio reproduction by enhancing a signal-to-noise ratio, better matching audio to the way the human brain processes audio, improving a user-machine interface, improving an experience of a human listening to the audio, or a combination thereof.

Numerous examples are disclosed in this application's text and drawings. Alternate examples can be devised without departing from the scope of this disclosure. Additionally, conventional elements of the current teachings may not be described in detail, or may be omitted, to avoid obscuring aspects of the current teachings.

The following list of abbreviations, acronyms, and terms is provided to assist in comprehending the current disclosure, and are not provided as limitations.

| |
|---|
| dB - Decibel |
| HPF - High Pass Filter |
| Hz - Hertz |
| LPF - Low Pass Filter |

Figure 1B:
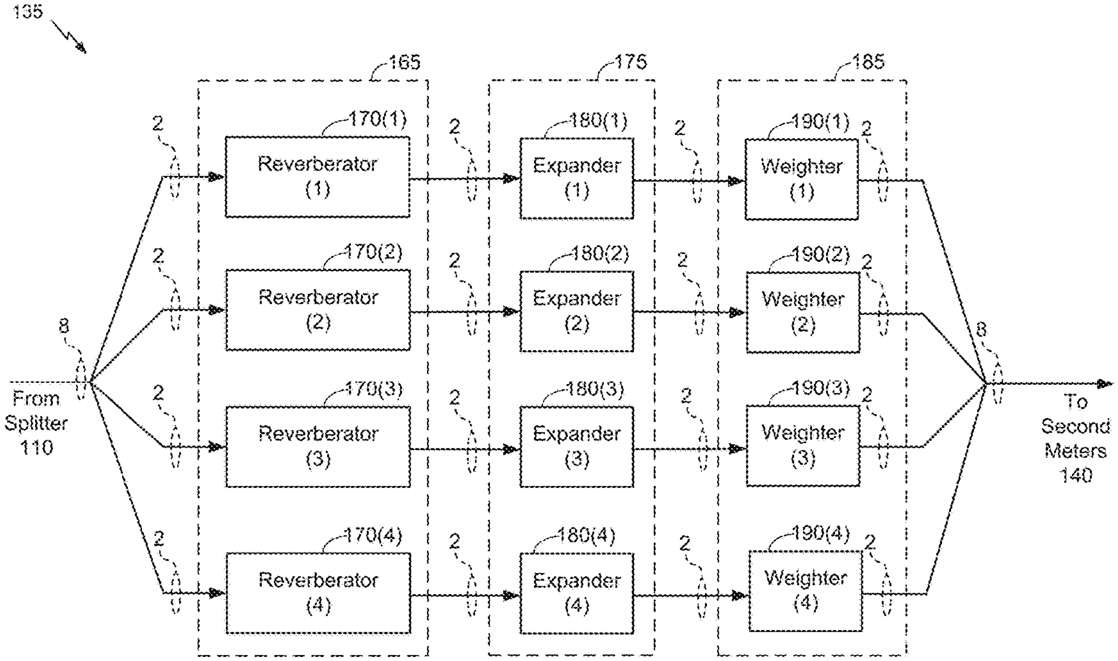
Figure 2:
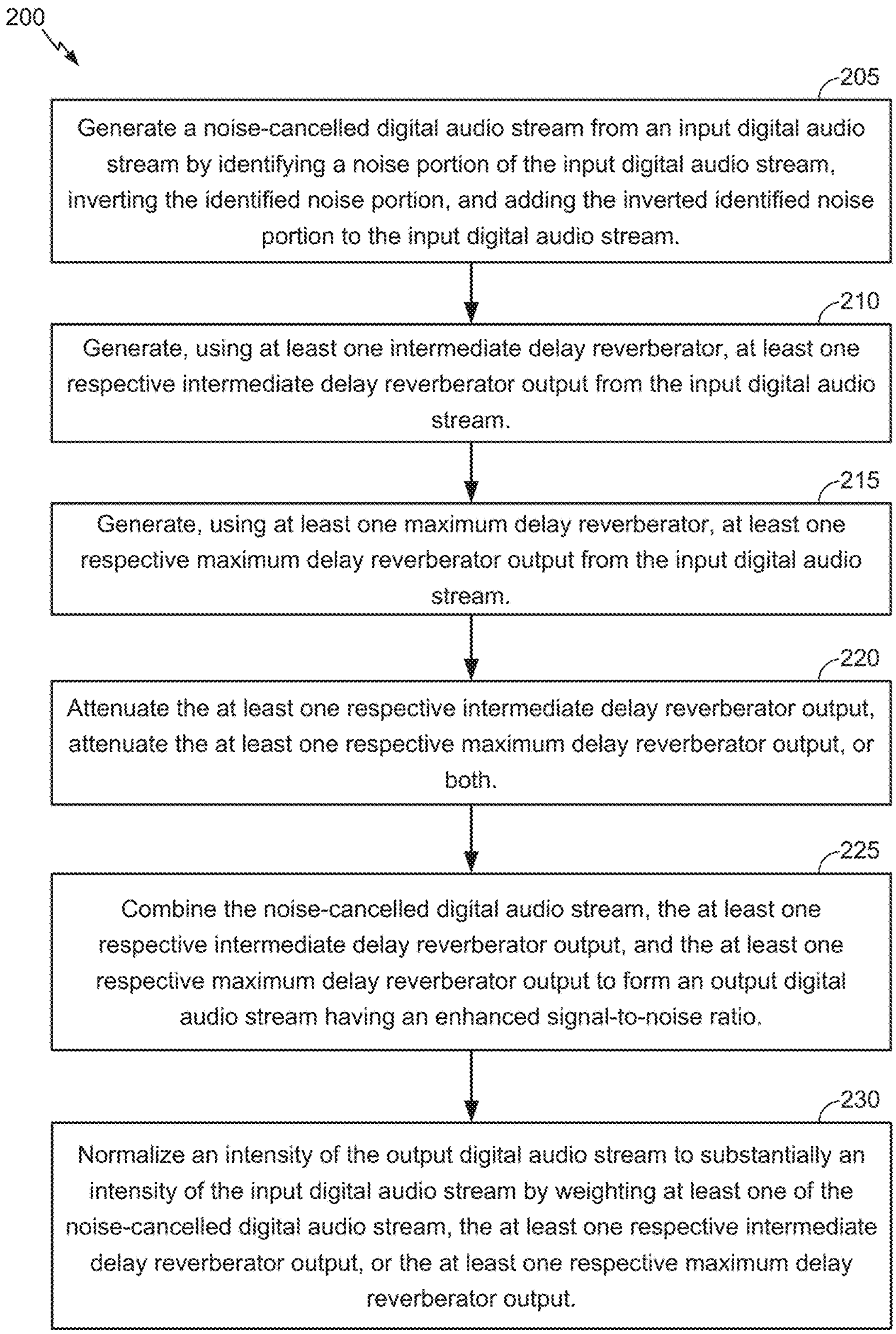
FIG. 2 depicts an example method for enhancing a signal-to-noise ratio.
Figure 3:
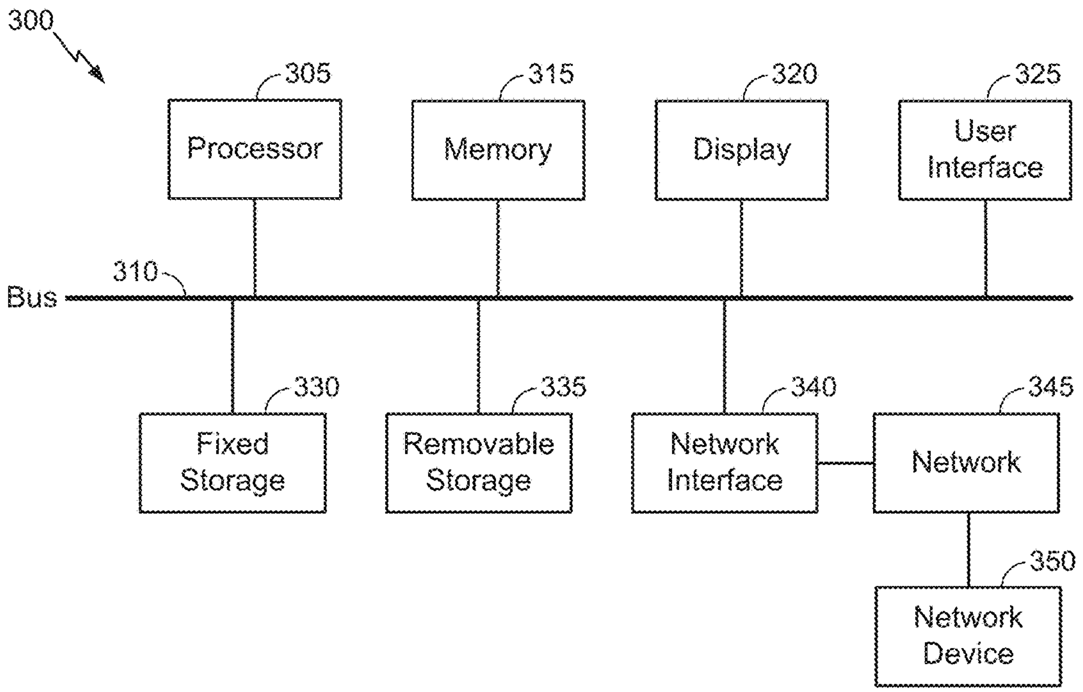
FIG. 3 depicts an example device suitable for implementing examples of the disclosed subject matter.

This description provides, with reference to FIGS. 1A, 1B, and 3, detailed descriptions of example apparatus for enhancing a signal-to-noise ratio. Detailed descriptions of an example method are provided in connection with FIG. 2.

FIGS. 1A-1B depict a block diagram of an example audio processing apparatus 100 configured to enhance a signal-to-noise ratio. The audio processing apparatus 100 can enhance a signal-to-noise ratio by performing at least a portion of the methods, sequences, algorithms, the like, or a combination thereof. The example audio processing apparatus 100 can be implemented at least in part directly in hardware, at least in part by a processor configured to execute stored instructions, or a combination of both. In addition, an electrical circuit of at least a portion of the audio processing apparatus 100 can be implemented as a digital logic circuit configured to perform a described action.

Referring to FIG. 1A, the audio processing apparatus 100 can include elements including an optional first low pass filter 105 (LPF), a splitter 110, a canceller 115, a first weighter 120, optional first meters 125, a summer 130, an imager 135, optional second meters 140, a second weighter 145, optional third meters 150, an optional high pass filter 155 (HPF), and an optional second low pass filter 160. These elements are described in further detail herein.

The optional first low pass filter 105 receives input audio, such as a digital audio stream or an analog audio stream, and filters the input audio. The first low pass filter 105 can be configured to receive a respective user input (e.g., from the user interface 325 depicted in FIG. 3) indicating a respective filter cutoff frequency. In examples, a bandpass filter or a high-pass filter can replace the first low pass filter 105 and filtering the input audio. In an example, the first low pass filter 105 has a cutoff frequency of substantially 18000 Hz.

The input audio can have a single channel or multiple channels. In an example, the input audio is two-channel stereo audio. In another example, the input audio is two-channel monaural audio. The two-channel configuration depicted in FIGS. 1A-1B is an illustrative example, and is not limiting.

The splitter 110 splits the output of the first low pass filter 105 into at least two paths—a first path to the canceller 115 and a second path to the imager 135. In an example, the audio sent to the canceller 115 and the images 135 is at least essentially identical. In an example, the splitter 110 splits monoaural input audio which is input to the audio processing apparatus 100 into multiple channels (e.g., a left channel and a right channel).

The canceller 115 generates noise-cancelled audio. The canceller 115 reduces noise to increase the effectivity of the audio processing apparatus 100. In an example, the canceller 115 identifies a noise portion of the audio input to the canceller 115, inverts the identified noise portion, and adds the inverted identified noise portion to the audio input to the canceller 115.

In an example, the audio input to the canceller 115 is attenuated (e.g., by −18 dB) to form intermediate audio characterized by reduced intensity (e.g., volume level). This effectively isolates meaningful information having a higher intensity from noise having a lower intensity. The intermediate audio is inverted and combined with the audio input to the canceller 115 to isolate a noise portion. The isolated noise portion is attenuated (e.g., by −18 dB). The isolated noise portion is then inverted and combined with the audio input to the canceller 115 to generate the noise-cancelled audio.

The noise-cancelled audio initially presents a sound in the output audio (i.e., "OUT" in FIG. 1A), and thus, for a human listener, is a timing reference for comparison of one or more subsequent echoes of the sound.

The optional first weighter 120 weights (e.g., adjusts by amplifying or attenuating) the noise-cancelled audio to balance audio intensity of the noise-cancelled audio which is input to the summer 130 with the intensity of audio input to the summer 130 from the second meters 140. Balancing the audio can prevent peaking and clipping in the output audio. In an example, the first weighter 120 attenuates the noise-cancelled audio by an amount in an inclusive range between substantially +1 dB to substantially −18 dB. In an example, the first weighter 120 attenuates the noise-cancelled audio by −3 dB. In an example, a weight applied by the first weighter 120 can be dynamic, with a change in the applied weight being based on a change in intensity of the input audio (e.g., at the input to the first LPF 105, the splitter 110, or the like). In another example, the applied weight can be user-selected and based on received selection information.

The optional first meters 125 measure intensity of the noise-cancelled audio and provide intensity information which can be displayed on a display, such as a display 320 depicted in FIG. 3.

The summer 130 forms output audio having the enhanced signal-to-noise ratio by combining (e.g., by adding) the noise-cancelled audio with at least one respective intermediate delay reverberator output, and at least one respective maximum delay reverberator output from the imager 135.

The imager 135 generates the at least one respective intermediate delay reverberator output, and the at least one respective maximum delay reverberator output. We now turn to FIG. 1B.

FIG. 1B illustrates an example block diagram of the imager 135, including a reverberator element 165 including one or more reverberators, such as reverberators 170(1)-(4), an expander element 175 including one or more expanders, such as expanders 180(1)-(4), and a weighter element 185 including one or more weighters, such as weighters 190(1)-(4).

The reverberator element 165 includes at least one reverberator which is configured to delay audio supplied to the summer 130 to produce at least one echo in the output audio. When humans listen to the output audio, they subconsciously listen for the echo and thus subconsciously focus on listening to, and for, meaningful echo information in the output audio. This focus causes humans to ignore noise in the output audio, which results in enhancing a signal-to-noise ratio. In an example, a reverberator can be replaced by a delay line. In another example, each reverberator can create a respective echo to simulate a reflection of the input audio from a simulated wall in a simulated room. In an example, one or more generated echoes includes a frequency within a human hearing range. In an example, the human hearing range can be within an inclusive range between 20 Hz to 24000 Hz. In another example, the human hearing range can be within an inclusive range between substantially 20 Hz to substantially 20000 Hz.

In the example in FIG. 1B, the reverberator element 165 has four reverberators 170(1)-170(4). The reverberator element 165 has two optional intermediate delay reverberators 170(1)-(2) and two maximum delay reverberators 170(3)-(4).

In examples, other quantities of reverberators can be implemented. An example can include one or more reverberators per channel, one or more reverberators per one or more respective delay times, or combinations thereof.

The intermediate delay reverberators 170(1)-(2) generate at least one respective intermediate delay reverberator output from the audio received from the splitter 110. The intermediate delay reverberator output provides audio which is an echo, relative to the noise-cancelled audio supplied to the summer 130. The intermediate delay reverberator output provides an echo having a shorter delay than an echo provided by the maximum delay reverberator output.

In an example, the intermediate delay reverberators 170(1)-(2) generate the at least one respective intermediate delay reverberator output at least in part by (1) weighting the audio received from the splitter 110 with a respective wet weight to produce respective wet-weighted audio, (2) reverberating the respective wet-weighted audio with the at least one intermediate delay reverberator to create at least one respective intervening output, (3) weighting the audio received from the splitter 110 with a respective dry weight to produce respective dry-weighted audio, and (4) producing the at least one respective intermediate delay reverberator output by combining the at least one respective intervening output with the respective dry-weighted audio.

The wet weight is an attenuation applied to audio which is subsequently reverberated. The dry weight is an attenuation applied to audio which is not reverberated, and is subsequently combined with reverberated audio. The wet weight, in cooperation with the dry weight, determines a proportion between a quantity of audio which is reverberated and a quantity of audio which is not reverberated. A ratio of the respective dry weight to the respective wet weight can be in an inclusive range between one-to-one and twenty-to-one.

The maximum delay reverberators 170(3)-(4) generate at least one respective maximum delay reverberator output from the audio received from the splitter 110. The maximum delay reverberator output provides audio which is an echo, relative to the noise-cancelled audio supplied to the summer 130. The maximum delay reverberator output provides an echo having a longer delay than an echo provided by the intermediate delay reverberator output.

In an example, maximum delay reverberators 170(3)-(4) generate the at least one respective maximum delay reverberator output at least in part by (A) weighting the audio received from the splitter 110 with a respective wet weight to produce a respective wet-weighted audio, (B) reverberating the respective wet-weighted audio with the at least one maximum delay reverberator to create at least one respective intervening output, (C) weighting the audio received from the splitter 110 with a respective dry weight to produce a respective dry-weighted audio stream, and (D) producing the at least one respective maximum delay reverberator output by combining the at least one respective intervening output with the respective dry-weighted audio. A ratio of the respective dry weight to the respective wet weight can be in an inclusive range between one-to-one and twenty-to-one.

In an example, generating the at least one respective maximum delay reverberator output includes the maximum delay reverberators 170(3)-(4) delaying the audio received from the splitter 110 by a maximum delay in an inclusive range between one sample cycle of the audio received from the splitter 110 to thirty sample cycles of the audio received from the splitter 110. A sample cycle, also known as a sampling interval and a sampling period, is a period of time between taking discrete samples of a continuous waveform to form the input digital audio stream. In an example, if the audio received from the splitter 110 has a sample rate of 44,100 Hz, then the sample cycle has a duration of 1/(44,100 seconds$^{-1}$)=0.0000226757 seconds. In examples, the audio received from the splitter 110 has a sample rate other than 44,100 Hz.

In an example, the maximum delay of the maximum delay reverberators 170(3)-(4) is long enough to provide the maximum delay reverberator output at a time to which human echolocation is sensitive. In an example, the maximum delay of the maximum delay reverberators 170(3)-(4) is short enough to provide the maximum delay reverberator output at a time to which a human does not consciously perceive reverberation of the audio.

The optional expander element 175 includes at least two expanders which are configured to attenuate respective left and right channels of the intermediate delay reverberator output and respective left and right channels of the maximum delay reverberator output. Reducing the respective intensities between left and right channels produces moving echoes (i.e., echoes with diminishing intensity). When humans listen to the output audio, they subconsciously focus on listening to the moving echoes, which induces focus on meaningful echo information in the output audio, thus enhancing a signal-to-noise ratio.

In the example in FIG. 1B, the expander element 175 includes four expanders. Expanders 180(1)-180(2) weight (e.g., attenuate or amplify) respective right and left channels of the intermediate delay reverberator output by different amounts. Expanders 180(3)-180(4) weight (e.g., attenuate or amplify) respective right and left channels of the maximum delay reverberator output by different amounts. In an example, the expanders 180(1)-180(4) attenuate by an amount in an inclusive range between 0.1% to 99.9%.

In an example, the expanders 180(1)-180(2) can attenuate the right channel of the intermediate delay reverberator output by 44% and can attenuate the left channel of the intermediate delay reverberator output by 17%. This combination of attenuations of the right channel of the intermediate delay reverberator output and the left channel of the intermediate delay reverberator output simulate an echo from a location in front, and slightly left of center of a listener. The expanders 180(3)-180(4) can attenuate the right channel of the maximum delay reverberator output by 90% and can attenuate the left channel of the maximum delay reverberator output by 0.5%. This combination of attenuations of the right channel of the intermediate delay reverberator output and the left channel of the intermediate delay reverberator output simulate an echo from a location from the left and slightly to the rear of the listener. These example attenuations are not limiting. In other examples, other attenuations can be implemented. For example, another attenuation can be implemented to simulate a respective echo from another location relative to a listener.

The optional weighter element 185 includes at least two weighters which are configured to attenuate (or amplify) the intermediate delay reverberator output and the maximum delay reverberator output. Reducing the respective intensities of the intermediate delay reverberator output and the maximum delay reverberator output, relative to the noise-cancelled audio supplied to the summer 130, produces fading echoes (i.e., echoes with diminishing intensity). When humans listen to the output audio, they subconsciously focus on listening to the fading echoes, which induces focus on meaningful echo information in the output audio, thus enhancing a signal-to-noise ratio. In an example, a weight applied by a respective weighter in the weighter element 185 can be dynamic, with a change in the applied weight being based on a change in intensity of the input audio. In another example, the applied weight can be user-selected and based on a received user selection of the applied weight.

In the example in FIG. 1B, the weighter element 185 includes four weighters—first and second weighters 190(1)-190(2) weight the intermediate delay reverberator output and third and fourth weighters 190(3)-190(4) weight the maximum delay reverberator output.

The first and second weighters 190(1)-190(2) and the third and fourth weighters 190(3)-190(4) weight (e.g., respectively amplify or respectively attenuate) a respective audio intensity of a respective channel. For example, the first weighter 190(1) and the third weighter 190(3) weight respective right channels, and the second weighter 190(2) and the fourth weighter 190(4) weight respective left channels. In a further example, the first weighter 190(1) and the third weighter 190(3) weight respective left channels, and the second weighter 190(2) and the fourth weighter 190(4) weight respective right channels.

In an example, the first and second weighters 190(1)-190(2) and the third and fourth weighters 190(3)-190(4) respectively attenuate by an amount in an inclusive range between substantially +1 dB to substantially −32 dB. In a non-limiting example, the weighters 190(1)-190(2) attenuate the intermediate delay reverberator output by −6 dB and the weighters 190(3)-190(4) weight the maximum delay reverberator output by −18 dB. In other examples, other attenuations can be implemented. For example, a user-selected attenuation can be implemented. In examples, the maximum delay reverberator output is attenuated more than the intermediate delay reverberator output to produce a fading series of echoes.

In an example, the intensity adjustments provided by the expander element 175 are performed by the weighter block 185. In another example, the intensity adjustments provided by the weighter block 185 are performed by the expander element 175.

Returning to FIG. 1A, the optional second meters 140 measure intensity of the at least one respective intermediate delay reverberator output, at least one respective maximum delay reverberator output, or both. The optional second meters 140 provide intensity information which can be displayed on a display, such as the display 320 in FIG. 3.

Again, the summer 130 forms the output audio having the enhanced signal-to-noise ratio by combining (e.g., by adding) the noise-cancelled audio originating in the canceller 115 with at least one respective intermediate delay reverberator output originating in the imager 135, and at least one respective maximum delay reverberator output originating in the imager 135. The combining of the noise-cancelled audio with the at least one respective intermediate delay reverberator output originating in the imager 135, and the at least one respective maximum delay reverberator output originating in the imager 135 can generate at least one overtone in the output audio.

In an example, the overtones are a product of an echo being combined (i.e., mixed) with the noise-cancelled audio. The combination can create the overtones (i.e., a harmonic resonance) due to periodic phase synchronization between respective waveforms of the echo and the noise-cancelled audio. The overtones generated by the audio processing apparatus 100 can include beat frequencies generated by the echo and the noise-cancelled audio beating against each other. The overtones generated by the echo can increase the intensity of meaningful information in the output audio at a time when the echo is present. For example, if the input audio includes meaningful information such as speech having a hard consonant, a hard syllable, etc., the overtones increase an intensity associated with the hard consonant, the hard syllable, etc. Accordingly, the intensity of meaningful information in the output audio increases relative to the intensity of noise in the output audio, which increases the signal-to-noise ratio. An empirical example of an impact of overtones on intensity of meaningful information in output audio is depicted and described herein in reference to FIGS. 5A-5B. An empirical example of an impact of overtones on signal-to-noise ratio in output audio is depicted and described herein in reference to FIGS. 6A-6B.

The optional second weighter 145 weights (e.g., attenuates or amplifies) an intensity of the audio from the summer 130 to normalize the intensity of the output audio to substantially match an intensity of the input audio. The second weighter 145 can receive an input (not shown, e.g., from the splitter 110) indicating the intensity of the input audio to use as a reference when normalizing. In an example, the second weighter 145 attenuates an intensity of the audio from the summer 130 by an amount in a range between substantially +1 dB to substantially −18 dB. In an example, the first weighter 120 attenuates the noise-cancelled audio by −3 dB. In an example, a weight applied by the second weighter 145 can be dynamic, with a change in the applied weight being based on a change in intensity of the input audio. In another example, the applied weight can be user-selected and based on a received user selection.

The optional third meters 150 measure a volume level and can provide volume level information which can be displayed on a display, such as the display 320 in FIG. 3.

The optional high pass filter 155 provides high-pass filtering. The high pass filter 155 can be configured to receive a respective user input (e.g., from the user interface 325 depicted in FIG. 3) indicating a respective filter cutoff frequency. In examples, a bandpass filter or a low-pass filter can replace the high pass filter 155 and filter the output audio.

The optional second low pass filter 160 provides low-pass filtering. The second low pass filter 160 can be configured to receive a respective user input (e.g., from the user interface 325 depicted in FIG. 3) indicating a respective filter cutoff frequency. In examples, a bandpass filter or a high-pass filter can replace the second low pass filter 160 and filter the output audio. In an example, the second low pass filter 160 has a cutoff frequency of substantially 18000 Hz.

In an example, the output audio from the audio processing apparatus 100 ("OUT" in FIG. 1A) (e.g., audio output from the second low pass filter 160) has a number of channels equal to the number of channels in the input audio which is input to the audio processing apparatus 100. In another example, the output audio from the audio processing apparatus 100 is not phase inverted relative to the input audio which is input to the audio processing apparatus 100.

The output audio from the audio processing apparatus 100 can be stored—for example, referring to FIG. 3, by memory 315, fixed storage 330, removable storage 335, network device 350, the like, or a combination thereof. The output audio from the audio processing apparatus 100 can be transmitted—for example, referring to FIG. 3, by user interface 325, network interface 340, the like, or a combination thereof. The output audio from the second low pass filter 160 can be reproduced—for example, referring to FIG. 3, by a speaker, headphones, an audio reproduction device, an audio processing device, the like, or a combination thereof coupled to the user interface 325, the network interface 340, the like, or a combination thereof.

In an example, one or more parts of the audio processing apparatus 100 can be a part of a system, communicatively coupled to a system, or both, where the system is a device configured to generate audio, convert audio, transmit audio, receive audio, store audio, process audio, reproduce audio, the like, or a combination thereof. In examples, the system can be a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, a drone aircraft, or a practicable combination thereof.

FIG. 2 depicts an example method which enhances a signal-to-noise ratio 200. The method for enhancing a signal-to-noise ratio 200 can be performed by the apparatus described hereby, such as the audio processing apparatus 100 in FIGS. 1A-1B, the example computing device 300 in FIG. 3, or a practicable combination thereof.

In block 205, a noise-cancelled digital audio stream is generated from an input digital audio stream by identifying a noise portion of the input digital audio stream, inverting the identified noise portion, and adding the inverted identified noise portion to the input digital audio stream.

The input digital audio stream can have a single channel or multiple channels. In an example, the input digital audio stream is two-channel stereo audio. In another example, the input digital audio stream is two-channel monaural audio. The two-channel configuration depicted in FIGS. 1A-1B is an illustrative example, and is not limiting.

In block 210, at least one respective intermediate delay reverberator output is generated from the input digital audio stream. The at least one respective intermediate delay reverberator output can be generated using at least one intermediate delay reverberator.

In an example, the at least one respective intermediate delay reverberator output is generated at least in part by weighting the input digital audio stream with a respective wet weight to produce a respective wet-weighted digital audio stream, reverberating the respective wet-weighted digital audio stream with the at least one intermediate delay reverberator to create at least one respective intervening output, weighting the input digital audio stream with a respective dry weight to produce a respective dry-weighted digital audio stream, and producing the at least one respective intermediate delay reverberator output by combining the at least one respective intervening output with the respective dry-weighted digital audio stream. The wet weight is an attenuation applied to audio which is subsequently reverberated. The dry weight is an attenuation applied to audio which is not reverberated, and is subsequently combined with reverberated audio. The wet weight, in cooperation with the dry weight, determines a proportion between a quantity of audio which is reverberated and a quantity of audio which is not reverberated. A ratio of the respective dry weight to the respective wet weight can be in a range between one-to-one and twenty-to-one.

In block 215, at least one respective maximum delay reverberator output is generated from the input digital audio stream. The at least one respective maximum delay reverberator output can be generated using at least one maximum delay reverberator.

In an example, the at least one respective maximum delay reverberator output is generated at least in part by weighting the input digital audio stream with a respective wet weight to produce a respective wet-weighted digital audio stream, reverberating the respective wet-weighted digital audio stream with the at least one maximum delay reverberator to create at least one respective intervening output, weighting the input digital audio stream with a respective dry weight to produce a respective dry-weighted digital audio stream, and producing the at least one respective maximum delay reverberator output by combining the at least one respective intervening output with the respective dry-weighted digital audio stream. A ratio of the respective dry weight to the respective wet weight can be in a range between one-to-one and twenty-to-one.

In an example, generating the at least one respective maximum delay reverberator output includes delaying the input digital audio stream by a maximum delay in an inclusive range between one sample cycle of the input digital audio stream to thirty sample cycles of the input digital audio stream. A sample cycle, also known as a sampling interval and a sampling period, is a period of time between taking discrete samples of a continuous waveform to form the input digital audio stream. In an example, if the input digital audio stream has a sample rate of 44,100 Hz, then the sample cycle has a duration of $1/(44{,}100\ \text{seconds}^{-1})=0.0000226757$ seconds. In an example, the maximum delay is long enough to provide the maximum delay reverberator output at a time to which human echolocation is sensitive. In an example, the maximum delay is short enough to provide the maximum delay reverberator output at a time to which a human does not consciously perceive reverberation of the audio.

In optional block 220, the at least one respective intermediate delay reverberator output is attenuated prior to the combining, the at least one respective maximum delay reverberator output is attenuated prior to the combining, or both.

In block 225, the noise-cancelled digital audio stream, the at least one respective intermediate delay reverberator output, and the at least one respective maximum delay reverberator output are combined to form an output digital audio stream having the enhanced signal-to-noise ratio.

In optional block 230, an intensity of the output digital audio stream is normalized to substantially an intensity of the input digital audio stream by weighting at least one of the noise-cancelled digital audio stream, the at least one respective intermediate delay reverberator output, or the at least one respective maximum delay reverberator output.

The blocks in FIG. 2 are not limiting of the examples. The blocks can be combined, the order can be rearranged, or both, as practicable.

Examples of the disclosed subject matter can be implemented in, and used with, hardware devices, network architectures, the like, and a combination thereof. FIG. 3 illustrates the example computing device 300 suitable for implementing examples of the disclosed subject matter. In an example, the computing device 300 can be a desktop computer, a laptop computer, a mobile device, a special-purpose computer, a non-generic computer, an electronic device described hereby (as is practicable), the like, or a combination thereof. In an example, the computing device 300 can be a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, a drone aircraft, the like, or a practicable combination thereof.

The computing device 300 can include a processor 305, a bus 310, the memory 315, the display 320, the user interface 325, the fixed storage device 330, the removable storage device 335, the network interface 340, the like, or a combination thereof.

The processor 305 is a hardware-implemented processing unit configured to control at least a portion of operation of the computing device 300. The processor 305 can perform logical and arithmetic operations based on processor-executable instructions stored within the memory 315. The processor 305 can be configured to execute instructions which cause the processor 305 to initiate at least a part of a method described hereby. In an example, the processor 305 can interpret instructions stored in the memory 315 to initiate at least a part of a method described hereby. In an example, the processor 305 can execute instructions stored in the memory 315 to initiate at least a part of a method described hereby. The instructions, when executed by the processor 305, can transform the processor 305 into a special-purpose processor that causes the processor to perform at least a part of a function described hereby. The processor 305 may also be referred to as a central processing unit (CPU), a special-purpose processor (e.g., a non-generic processor), or both.

The processor 305 can comprise or be a component of a physical processing system implemented with one or more processors. The processor 305 can be implemented with at least a portion of: a microprocessor, a microcontroller, a digital signal processor (DSP) integrated circuit, a field programmable gate array (FPGA), a programmable logic device (PLD), an application-specific integrated circuit (ASIC), a controller, a state machine, a gated logic circuit, a discrete hardware component, a dedicated hardware finite state machine, a suitable physical device configured to manipulate information (e.g., calculating, logical operations, the like, or a combination thereof), the like, or a combination thereof.

The bus 310 couples components of the computing device 300. The bus 310 can enable information communication between the processor 305 and one or more components coupled to the processor 305. The bus 310 can include a data bus, a power bus, a control signal bus, a status signal bus, the like, or a combination thereof. In an example, the components of the computing device 300 can be coupled together to communicate with each other using a different suitable mechanism.

The memory 315 generally represents any type or form of volatile storage device, non-volatile storage device, medium, the like, or a combination thereof. The memory 315 is capable of storing data, processor-readable instructions, the like, or a combination thereof. In an example, the memory 315 can store data, load data, maintain data, or a combination thereof. In an example, the memory 315 can store processor-readable instructions, load processor-readable instructions, maintain processor-readable instructions, or a combination thereof. The memory 315 can be a main memory configured to store an operating system, an application program, the like, or a combination thereof. The memory 315 can be configured to store a basic input-output system (BIOS) which can control basic hardware operation such as interaction of the processor 305 with peripheral components. The memory 310 can also include a non-transitory machine-readable medium configured to store software. Software can mean any type of instructions, whether referred to as at least one of software, firmware, middleware, microcode, hardware description language, the like, or a combination thereof. Processor-readable instructions can include code (e.g., in source code format, in binary code format, executable code format, or in any other suitable code format).

The memory 315 can include at least one of read-only memory (ROM), random access memory (RAM), a flash memory, a cache memory, an erasable programmable read-only memory (EPROM), an electrically erasable programmable read-only memory (EEPROM), a register, a hard disk drive (HDD), a solid-state drive (SSD), an optical disk drive, other memory, the like, or a combination thereof which is configured to store information (e.g., data, processor-readable instructions, software, the like, or a combination thereof) and is configured to provide the information to the processor 305.

The video display 320 can include a component configured to visually convey information to a user of the computing device 300. In examples, the video display 320 is a display screen, such as a light-emitting diode (LED) screen.

The user interface 325 can include user devices such as a switch, a keypad, a touch screen, a microphone, a speaker, an audio reproduction device, a jack for coupling the computing device to an audio reproduction device, the like, or a combination thereof. The user interface 325 can optionally include a user interface controller. The user interface 325 can include a component configured to convey information to a user of the computing device 300, a component configured to receive information from the user of the computing device 300, or both.

The fixed storage device 330 can include one or more hard drive, flash storage device, the like, or a combination thereof. The fixed storage device 330 can be an information storage device which is not configured to be removed during use. The fixed storage device 330 can optionally include a fixed storage device controller. The fixed storage device 330 can be integral with the computing device 300 or can be separate and accessed through an interface.

The removable storage device 335 can be integral with the computing device 300 or can be separate and accessed through other interfaces. The removable storage device 335 can be an information storage device which is configured to be removed during use, such as a memory card, a jump drive, a flash storage device, an optical disk, the like, or a combination thereof. The removable storage device 335 can optionally include a removable storage device controller. The removable storage device 335 can be integral with the computing device 300 or can be separate and accessed through an interface.

Non-transient computer-executable instructions configured to cause a processor to implement at least an aspect of the present disclosure can be stored on a computer-readable storage medium such as one or more of the memory 315, the fixed storage device 330, the removable storage device 335, a remote storage location, the like, or a combination thereof.

The network interface 340 can couple the computing device 300 to a network 345 and enable exchanging information between the computing device 300 and the network 345. For example, the network interface 340 can enable the computing device 300 to communicate with one or more other network devices 350. The network interface 340 can couple to the network 345 using any suitable technique and any suitable protocol. Example techniques and protocols the network interface 340 can be configured to implement include digital cellular telephone, WiFi™, Bluetooth®, near-field communications (NFC), the like, or a combination thereof.

The network 345 can couple the computing device 300 to one or more other network devices. The network 345 can enable exchange of information between the computing device 300 and the one or more other network devices 350. The network 345 can include one or more private networks, local networks, wide-area networks, the Internet, other communication networks, the like, or a combination thereof. In an example, the network 345 is a wired network, a wireless network, an optical network, the like, or a combination thereof.

The one or more other network devices 350 can store computer-readable instructions configured to cause a processor (e.g., the processor 305) to initiate performing at least a portion of a method described hereby. In an example, the one or more other network devices 350 can store a first digital audio file. The first digital audio file can be received by the processor 305 and processed using at least a portion of techniques described hereby. In another example, a second digital audio file can be created by the processor 305 using techniques described hereby and stored in the fixed storage device 330, the removable storage device 335, the one or more other network devices 350, the like, or a combination thereof.

The one or more other network devices 350 can include a server, a storage medium, the like, or a combination thereof. When the one or more other network devices 350 is a server, the first digital audio file can be received by the server and processed using at least a portion of techniques described hereby. In another example, a second digital audio file can be created by the server using techniques described hereby and stored in the fixed storage device 330, the removable storage device 335, the one or more other network devices 350, the like, or a combination thereof.

In examples, the one or more other network devices 350 include a speaker, headphones, an audio reproduction device, an audio processing device, the like, or a combination thereof. Thus, audio processed using the techniques described hereby can be reproduced via the speaker, the headphones, the audio reproduction device, or a combination thereof. In an example, the reproducing can be performed for a human.

All of the components illustrated in FIG. 3 need not be present to practice the present disclosure. Further, the components can be coupled in different ways from those illustrated.

FIGS. 4, 5A-5B, and 6A-6B depict non-limiting empirical examples relating to implementing an embodiment of the audio processing apparatus 100.

Figure 4:
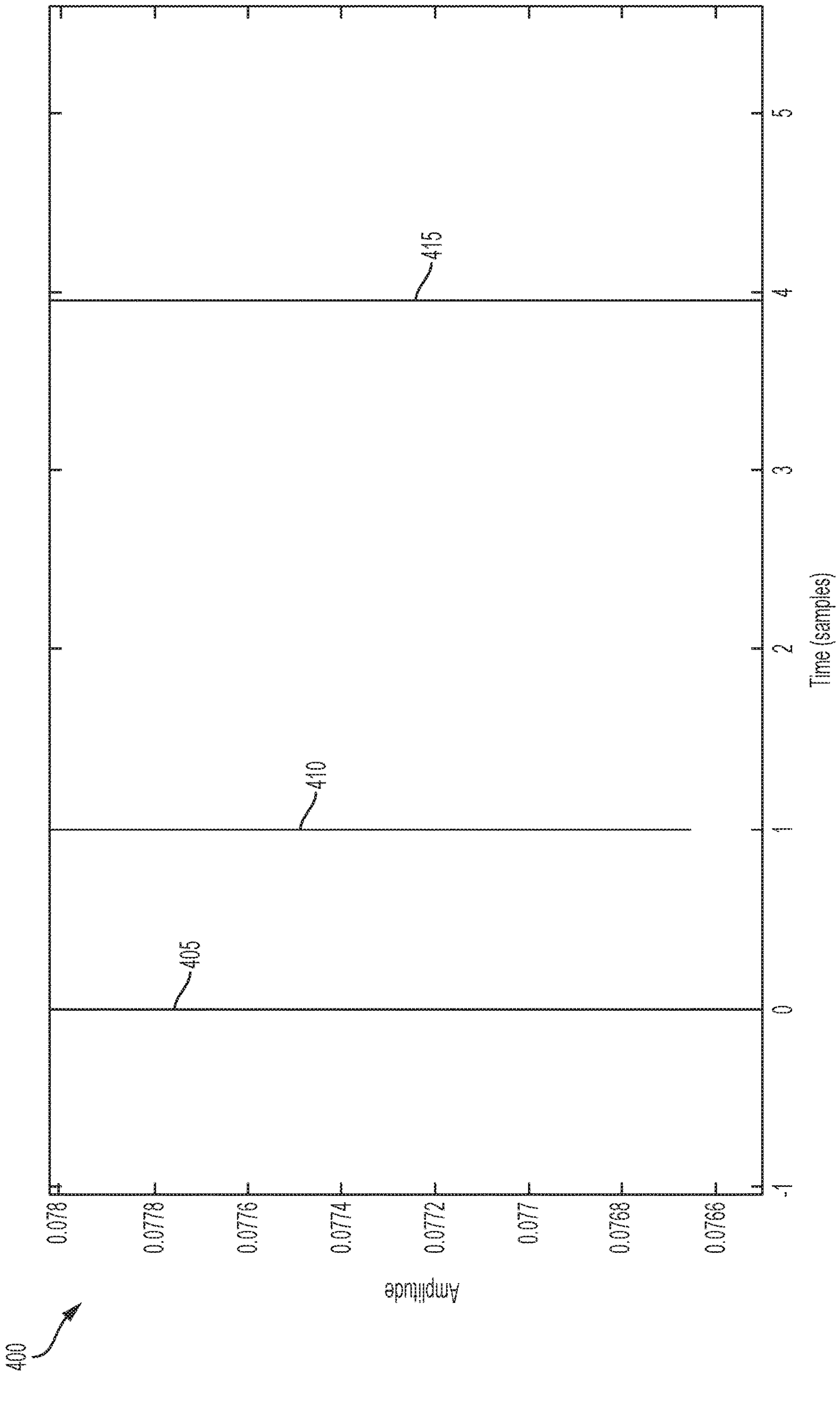
FIG. 4 depicts an example impulse response of an example audio processing apparatus.

FIG. 4 depicts a non-limiting example impulse response 400 of the embodiment of the audio processing apparatus 100. Further, FIG. 4 depicts that the example impulse response 400 of the embodiment of the audio processing apparatus 100 is linear. At substantially time zero, the embodiment of the audio processing apparatus 100 receives input audio having an input impulse 405. The input impulse 405 triggers the embodiment of the audio processing apparatus 100 to generate, at substantially time one, a response 410 in the output audio that includes noise-cancelled audio. The input impulse 405 also triggers the embodiment of the audio processing apparatus 100 to generate an echo 415 of the input impulse 405. In response, the embodiment of the audio processing apparatus 100 generates the echo 415 at substantially time four. In the example of FIG. 4, time is measured in sample cycles. Thus, noise-cancelled audio is output substantially one sample cycle after the embodiment of the audio processing apparatus 100 receives the input impulse 405. The echo 415 is output substantially three sample cycles after the embodiment of the audio processing apparatus 100 receives the input impulse 405.

Figure 5A:
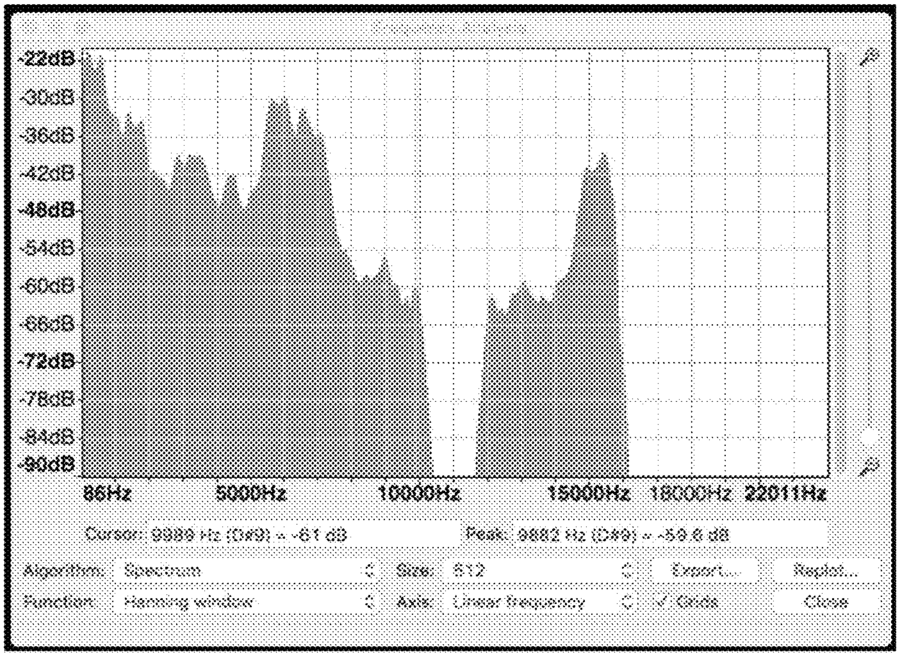
FIG. 5A depicts an example spectrum of example input audio.
Figure 5B:
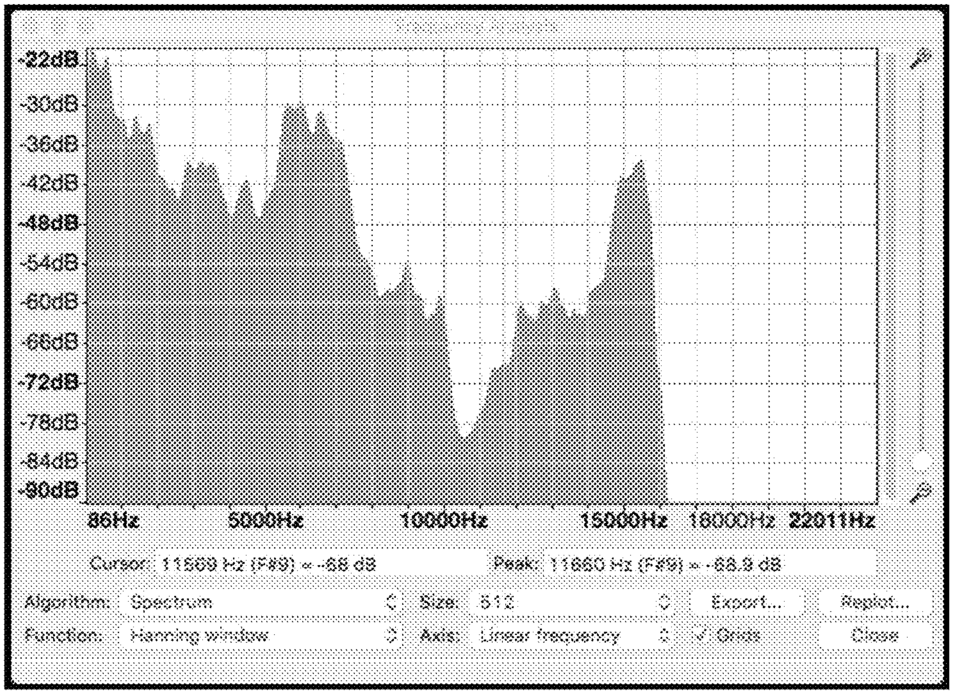
FIG. 5B depicts an example spectrum of example output audio including overtone frequencies.

FIGS. 5A-5B depict empirical examples showing the example embodiment of the audio processing apparatus 100 can increase a signal-to-noise ratio. The signal-to-noise ratio increases because the example embodiment of the audio processing apparatus 100 increases intensity of meaningful information in the output signal by generating overtones from echoes. FIG. 5A depicts a spectrum of example input audio 500 which is input to the embodiment of the audio processing apparatus 100. The spectrum of example input audio 500 depicts input audio lacking intensity from approximately 10500 Hz to approximately 11500 Hz. The example embodiment of the audio processing apparatus 100 generates echoes and respective overtones from the input audio. We now turn to FIG. 5B, which depicts a spectrum of example output audio 505 including overtones created by the audio processing apparatus 100. As can be seen in FIG. 5B, the overtones increase an intensity of meaningful information at frequencies including the range from approximately 10500 Hz to approximately 11500 Hz, thus increasing the signal-to-noise ratio of the example output audio.

Figure 6A:
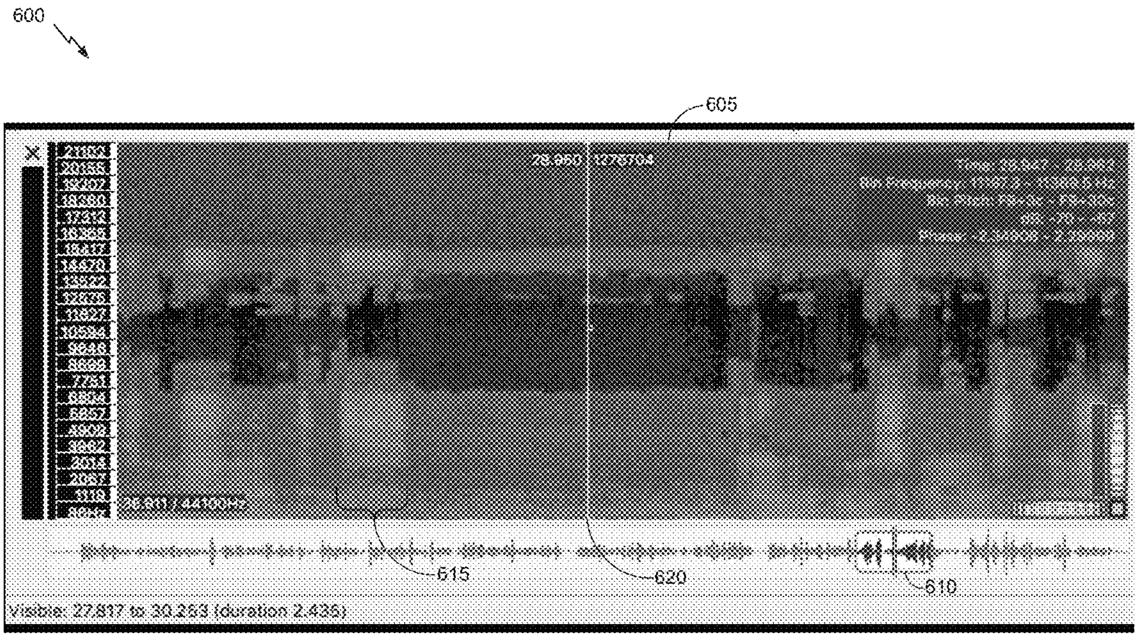
FIG. 6A depicts example measurements of example input audio.
Figure 6B:
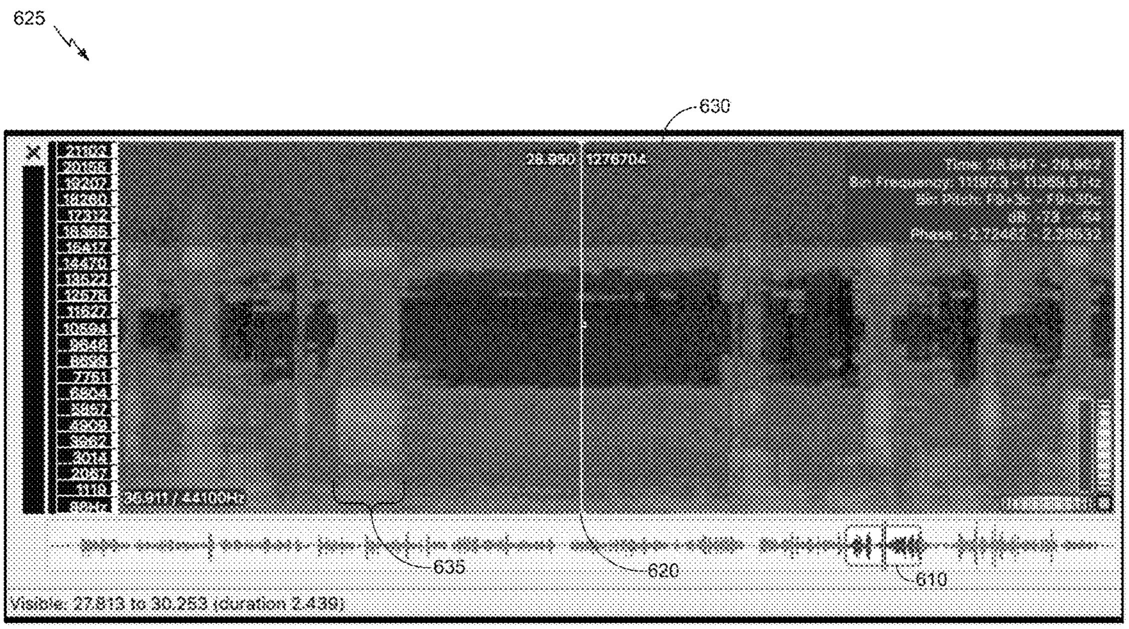
FIG. 6B depicts example measurements of example output audio having an improved signal-to-noise ratio.

FIGS. 6A-6B depict empirical examples showing the example embodiment of the audio processing apparatus 100 can increase the signal-to-noise ratio in output audio. FIGS. 6A-6B also depict an empirical example of an impact of overtones on signal-to-noise ratio in the output audio. The examples in FIGS. 6A-6B are not limiting.

FIG. 6A depicts input measurements 600 of example empirical input audio which can be input to the embodiment of the audio processing apparatus 100. The input measurements 600 include an input heatmap 605 indicating intensity of the input audio at different times and frequencies. The horizontal axis of the input heatmap 605 indicates time, while the vertical axis of the input heatmap 605 indicates frequency. The selection box 610 indicates a selected portion of the input audio whose characteristics are displayed by the input heatmap 605.

The input heatmap 605 depicts that the input audio includes meaningful information 615 during a portion of time. The input heatmap 605 also depicts the meaningful information 615 has low intensities in the frequencies between approximately 9646 Hz to approximately 12575 Hz, relative to respective intensities occurring at other frequencies outside this range during the portion of time.

FIG. 6A also depicts the signal-to-noise ratio of the input audio, at a time indicated by a cursor 620, as having a signal portion of −67 dB and a noise portion of −70 dB.

FIG. 6B depicts output measurements 625 of example empirical output audio from the embodiment of the audio processing apparatus 100 resulting from the example empirical input audio from FIG. 6A being input to the example embodiment of the audio processing apparatus 100. The output measurements 625 include an output heatmap 630 indicating intensity of the output audio at different times and frequencies. The horizontal axis of the output heatmap 630 indicates time, while the vertical axis of the output heatmap 630 indicates frequency. The selection box 610 indicates that the selected portion of the input audio whose characteristics are displayed by the output heatmap 630 is substantially the same as the selected portion of the input audio whose characteristics are displayed by the input heatmap 605.

The output heatmap 630 depicts that the output audio includes meaningful information 635 during the portion of time. The output heatmap 630 also depicts the meaningful information 635 has a higher intensity in the frequencies between approximately 9646 Hz to approximately 12575 Hz, relative to the respective lower intensities depicted in FIG. 6A. The meaningful information 635 has a higher intensity in the frequencies between approximately 9646 Hz to approximately 12575 Hz due to overtones, generated by the example embodiment of the audio processing apparatus 100, at the frequencies between approximately 9646 Hz to approximately 12575 Hz.

Thus, because the intensity of the meaningful information 635 increases at the frequencies between approximately 9646 Hz to approximately 12575 Hz, the signal-to-noise ratio of the output audio is improved, relative to the signal-to-noise ratio of the input audio.

FIG. 6B also depicts the signal-to-noise ratio of the output audio at the time indicated by the cursor 620 as having a signal portion of −64 dB and a noise portion of −73 dB. Thus, the signal-to-noise ratio of the output audio is improved, relative to the signal-to-noise ratio of the input audio, with the signal intensity of the output audio changed by +3 dB relative to the input audio, and the noise intensity of the output audio changed by −3 dB relative to the input audio.

As used hereby, the term "example" means "serving as an example, instance, or illustration". Any example described as an "example" is not necessarily to be construed as preferred or advantageous over other examples. Likewise, the term "examples" does not require all examples include the discussed feature, advantage, or mode of operation. Use of the terms "in one example," "an example," "in one feature," and/or "a feature" in this specification does not necessarily refer to the same feature and/or example. Furthermore, a particular feature and/or structure can be combined with one or more other features and/or structures. Moreover, at least a portion of the apparatus described hereby can be configured to perform at least a portion of a method described hereby.

It should be noted the terms "connected," "coupled," and any variant thereof, mean any connection or coupling between elements, either direct or indirect, and can encompass a presence of an intermediate element between two elements which are "connected" or "coupled" together via the intermediate element. Coupling and connection between the elements can be physical, logical, or a combination thereof. Elements can be "connected" or "coupled" together, for example, by using one or more wires, cables, printed electrical connections, electromagnetic energy, and the like. The electromagnetic energy can have a wavelength at a radio frequency, a microwave frequency, a visible optical frequency, an invisible optical frequency, and the like, as practicable. These are several non-limiting and non-exhaustive examples.

The term "signal" can include any signal such as a data signal, an audio signal, a video signal, a multimedia signal, an analog signal, a digital signal, and the like. Information and signals described hereby can be represented using any of a variety of different technologies and techniques. For example, data, an instruction, a process step, a process block, a command, information, a signal, a bit, a symbol, and the like which are referred to hereby can be represented by a voltage, a current, an electromagnetic wave, a magnetic field, a magnetic particle, an optical field, an optical particle, and/or any practical combination thereof, depending at least in part on the particular application, at least in part on the desired design, at least in part on the corresponding technology, and/or at least in part on like factors.

A reference using a designation such as "first," "second," and so forth does not limit either the quantity or the order of those elements. Rather, these designations are used as a convenient method of distinguishing between two or more elements or instances of an element. Thus, a reference to first and second elements does not mean only two elements can be employed, or the first element must necessarily precede the second element. Also, unless stated otherwise, a set of elements can comprise one or more elements. In addition, terminology of the form "at least one of: A, B, or C" or "one or more of A, B, or C" or "at least one of the group consisting of A, B, and C" used in the description or the claims can be interpreted as "A or B or C or any combination of these elements". For example, this terminology can include A, or B, or C, or A and B, or A and C, or A and B and C, or 2A, or 2B, or 2C, and so on.

The terminology used hereby is for the purpose of describing particular examples only and is not intended to be limiting. As used hereby, the singular forms "a," "an," and "the" include the plural forms as well, unless the context clearly indicates otherwise. In other words, the singular portends the plural, where practicable. Further, the terms "comprises," "comprising," "includes," and "including," specify a presence of a feature, an integer, a step, a block, an operation, an element, a component, and the like, but do not necessarily preclude a presence or an addition of another feature, integer, step, block, operation, element, component, and the like.

Those of skill in the art will appreciate the example logical blocks, elements, modules, circuits, and steps described in the examples disclosed hereby can be implemented as electronic hardware, computer software, or combinations of both, as practicable. To clearly illustrate this interchangeability of hardware and software, example components, blocks, elements, modules, circuits, and steps have been described hereby generally in terms of their functionality. Whether such functionality is implemented as hardware or software depends upon the particular application and design constraints imposed on an overall system. Skilled artisans can implement the described functionality in different ways for each particular application, but such implementation decisions should not be interpreted as causing a departure from the scope of the present disclosure.

At least a portion of the methods, sequences, algorithms or a combination thereof which are described in connection with the examples disclosed hereby can be embodied directly in hardware, in instructions executed by a processor (e.g., a processor described hereby), or in a combination thereof. In an example, a processor includes multiple discrete hardware components. Instructions can reside in a non-transient storage medium (e.g., a memory device), such as a random-access memory (RAM), a flash memory, a read-only memory (ROM), an erasable programmable read-only memory (EPROM), an electrically erasable programmable read-only memory (EEPROM), a register, a hard disk, a removable disk, a compact disc read-only memory (CD-ROM), any other form of storage medium, the like, or a combination thereof. An example storage medium (e.g., a memory device) can be coupled to the processor so the processor can read information from the storage medium, write information to the storage medium, or both. In an example, the storage medium can be integral with the processor.

Further, examples provided hereby are described in terms of sequences of actions to be performed by, for example, one or more elements of a computing device. The actions described hereby can be performed by a specific circuit (e.g., an application specific integrated circuit (ASIC)), by instructions being executed by one or more processors, or by a combination of both. Additionally, a sequence of actions described hereby can be entirely within any form of non-transitory computer-readable storage medium having stored thereby a corresponding set of computer instructions which, upon execution, cause an associated processor (such as a special-purpose processor) to perform at least a portion of a function described hereby. Additionally, a sequence of actions described hereby can be entirely within any form of non-transitory computer-readable storage medium having stored thereby a corresponding set of instructions which, upon execution, configure the processor to create specific logic circuits. Thus, examples may be in a number of different forms, all of which have been contemplated to be within the scope of the disclosure. In addition, for each of the examples described hereby, a corresponding electrical circuit of any such examples may be described hereby as, for example, "a logic circuit configured to" perform a described action.

In an example, when a general-purpose computer (e.g., a processor) is configured to perform at least a portion of a method described hereby, then the general-purpose computer becomes a special-purpose computer which is not generic and is not a general-purpose computer. In an example, loading a general-purpose computer with special programming can cause the general-purpose computer to be configured to perform at least a portion of a method described hereby. In an example, a combination of two or more related method steps disclosed hereby forms a sufficient algorithm. In an example, a sufficient algorithm constitutes special programming. In an example, special programming constitutes any software which can cause a computer (e.g., a general-purpose computer, a special-purpose computer, etc.) to be configured to perform one or more functions, features, steps algorithms, blocks, or a combination thereof, as disclosed hereby.

At least one example provided hereby can include a non-transitory (i.e., a non-transient) machine-readable medium and/or a non-transitory (i.e., a non-transient) computer-readable medium storing processor-executable instructions configured to cause a processor (e.g., a special-purpose processor) to transform the processor and any other cooperating devices into a machine (e.g., a special-purpose processor) configured to perform at least a part of a function described hereby, at least a part of a method described hereby, the like, or a combination thereof. Performing at least a part of a function described hereby can include initiating at least a part of a function described hereby, at least a part of a method described hereby, the like, or a combination thereof. In an example, execution of the stored instructions can transform a processor and any other cooperating devices into at least a part of an apparatus described hereby. A non-transitory (i.e., a non-transient) machine-readable medium specifically excludes a transitory propagating signal. Further, one or more examples can include a computer-readable medium embodying at least a part of a function described hereby, at least a part of a method described hereby, the like, or a combination thereof. A non-transitory (i.e., a non-transient) machine-readable medium specifically excludes a transitory propagating signal.

Nothing stated or depicted in this application is intended to dedicate any component, step, block, element, feature, object, benefit, advantage, or equivalent to the public, regardless of whether the component, step, block, element, feature, object, benefit, advantage, or the equivalent is recited in the claims. While this disclosure describes examples, changes and modifications can be made to the examples disclosed hereby without departing from the scope defined by the appended claims. A feature from any of the provided examples can be used in combination with one another feature from any of the provided examples in accordance with the general principles described hereby. The present disclosure is not intended to be limited to the specifically disclosed examples alone.

What is claimed is:

1. An apparatus configured to enhance a signal-to-noise ratio, comprising:

- a physical processor; and
- a memory communicably coupled to the physical processor and storing instructions configured to cause the physical processor to:
  - initiate generating a noise-cancelled digital audio stream from an input digital audio stream, wherein the generating the noise-cancelled digital audio stream includes:
    - identifying a noise portion of the input digital audio stream;
    - inverting the identified noise portion; and
    - adding the inverted identified noise portion to the input digital audio stream;
  - initiate generating, using at least one intermediate delay reverberator, at least one respective intermediate delay reverberator output from the input digital audio stream;
  - initiate generating, using at least one maximum delay reverberator, at least one respective maximum delay reverberator output from the input digital audio stream; and
  - initiate combining the noise-cancelled digital audio stream, the at least one respective intermediate delay reverberator output, and the at least one respective maximum delay reverberator output to form an output digital audio stream having the enhanced signal-to-noise ratio.

2. The apparatus of claim 1, wherein the memory further stores instructions configured to cause the processor to initiate normalizing an intensity of the output digital audio stream to substantially an intensity of the input digital audio stream by weighting at least one of the noise-cancelled digital audio stream, the at least one respective intermediate delay reverberator output, or the at least one respective maximum delay reverberator output.

3. The apparatus of claim 1, wherein the generating at least one respective intermediate delay reverberator output includes:

- weighting the input digital audio stream with a respective wet weight to produce a respective wet-weighted digital audio stream;
- reverberating the respective wet-weighted digital audio stream with the at least one intermediate delay reverberator to create at least one respective intervening output;
- weighting the input digital audio stream with a respective dry weight to produce a respective dry-weighted digital audio stream; and
- producing the at least one respective intermediate delay reverberator output by combining the at least one respective intervening output with the respective dry-weighted digital audio stream.

4. The apparatus of claim 3, wherein a ratio of the respective dry weight to the respective wet weight is in an inclusive range between one-to-one and twenty-to-one.

5. The apparatus of claim 1, wherein the generating at least one respective maximum delay reverberator output includes:

- weighting the input digital audio stream with a respective wet weight to produce a respective wet-weighted digital audio stream;
- reverberating the respective wet-weighted digital audio stream with the at least one maximum delay reverberator to create at least one respective intervening output;
- weighting the input digital audio stream with a respective dry weight to produce a respective dry-weighted digital audio stream; and
- producing the at least one respective maximum delay reverberator output by combining the at least one respective intervening output with the respective dry-weighted digital audio stream.

6. The apparatus of claim 5, wherein a ratio of the respective dry weight to the respective wet weight is in an inclusive range between one-to-one and twenty-to-one.

7. The apparatus of claim 1, wherein the generating at least one respective maximum delay reverberator output includes delaying the input digital audio stream by a maximum delay in an inclusive range between one sample cycle of the input digital audio stream to thirty sample cycles of the input digital audio stream.

8. The apparatus of claim 1, wherein the memory further stores instructions configured to cause the processor to at least one of:

- initiate attenuating, prior to initiating the combining, the at least one respective intermediate delay reverberator output; or
- initiate attenuating, prior to initiating the combining, the at least one respective maximum delay reverberator output.

9. The apparatus of claim 1, wherein the apparatus is a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft.

10. The apparatus of claim 1, wherein the physical processor is at least one of a microprocessor, a microcontroller, a digital signal processor, a field programmable gate array, a programmable logic device, an application-specific integrated circuit, a controller, a non-generic special-purpose processor, a state machine, a gated logic device, a discrete hardware component, or a dedicated hardware finite state machine, or a combination thereof.

11. A method for enhancing a signal-to-noise ratio, the method comprising:

generating a noise-cancelled digital audio stream from an input digital audio stream by:

identifying a noise portion of the input digital audio stream;

inverting the identified noise portion; and adding the inverted identified noise portion to the input digital audio stream;

generating, using at least one intermediate delay reverberator, at least one respective intermediate delay reverberator output from the input digital audio stream;

generating, using at least one maximum delay reverberator, at least one respective maximum delay reverberator output from the input digital audio stream; and combining the noise-cancelled digital audio stream, the at least one respective intermediate delay reverberator output, and the at least one respective maximum delay reverberator output to form an output digital audio stream having the enhanced signal-to-noise ratio.

12. The method of claim 11, further comprising normalizing an intensity of the output digital audio stream to substantially an intensity of the input digital audio stream by weighting at least one of the noise-cancelled digital audio stream, the at least one respective intermediate delay reverberator output, or the at least one respective maximum delay reverberator output.

13. The method of claim 11, wherein the generating at least one respective intermediate delay reverberator output includes:

weighting the input digital audio stream with a respective wet weight to produce a respective wet-weighted digital audio stream;

reverberating the respective wet-weighted digital audio stream with the at least one intermediate delay reverberator to create at least one respective intervening output;

weighting the input digital audio stream with a respective dry weight to produce a respective dry-weighted digital audio stream; and producing the at least one respective intermediate delay reverberator output by combining the at least one respective intervening output with the respective dry-weighted digital audio stream.

14. The method of claim 13, wherein a ratio of the respective dry weight to the respective wet weight is in an inclusive range between one-to-one and twenty-to-one.

15. The method of claim 11, wherein the generating at least one respective maximum delay reverberator output includes:

weighting the input digital audio stream with a respective wet weight to produce a respective wet-weighted digital audio stream;

reverberating the respective wet-weighted digital audio stream with the at least one maximum delay reverberator to create at least one respective intervening output;

weighting the input digital audio stream with a respective dry weight to produce a respective dry-weighted digital audio stream; and producing the at least one respective maximum delay reverberator output by combining the at least one respective intervening output with the respective dry-weighted digital audio stream.

16. The method of claim 15, wherein a ratio of the respective dry weight to the respective wet weight is in an inclusive range between one-to-one and twenty-to-one.

17. The method of claim 11, wherein the generating at least one respective maximum delay reverberator output includes delaying the input digital audio stream by a maximum delay in an inclusive range between one sample cycle of the input digital audio stream to thirty sample cycles of the input digital audio stream.

18. The method of claim 11, further comprising at least one of:

attenuating, prior to the combining, the at least one respective intermediate delay reverberator output; or attenuating, prior to the combining, the at least one respective maximum delay reverberator output.

19. A non-transitory computer-readable medium, comprising processor-executable instructions stored thereon configured to cause a processor to:

initiate generating a noise-cancelled digital audio stream from an input digital audio stream, wherein the generating the noise-cancelled digital audio stream includes:

identifying a noise portion of the input digital audio stream;

inverting the identified noise portion; and adding the inverted identified noise portion to the input digital audio stream;

initiate generating, using at least one intermediate delay reverberator, at least one respective intermediate delay reverberator output from the input digital audio stream;

initiate generating, using at least one maximum delay reverberator, at least one respective maximum delay reverberator output from the input digital audio stream; and initiate combining the noise-cancelled digital audio stream, the at least one respective intermediate delay reverberator output, and the at least one respective maximum delay reverberator output to form an output digital audio stream having the enhanced signal-to-noise ratio.

20. The non-transitory computer-readable medium of claim 19, wherein the processor-executable instructions further include instructions configured to cause the processor to initiate normalizing an intensity of the output digital audio stream to substantially an intensity of the input digital audio stream by weighting at least one of the noise-cancelled digital audio stream, the at least one respective intermediate delay reverberator output, or the at least one respective maximum delay reverberator output.

21. The non-transitory computer-readable medium of claim 19, wherein the generating at least one respective intermediate delay reverberator output includes:

weighting the input digital audio stream with a respective wet weight to produce a respective wet-weighted digital audio stream;

reverberating the respective wet-weighted digital audio stream with the at least one intermediate delay reverberator to create at least one respective intervening output;

weighting the input digital audio stream with a respective dry weight to produce a respective dry-weighted digital audio stream; and producing the at least one respective intermediate delay reverberator output by combining the at least one respective intervening output with the respective dry-weighted digital audio stream.

22. The non-transitory computer-readable medium of claim 21, wherein a ratio of the respective dry weight to the respective wet weight is in an inclusive range between one-to-one and twenty-to-one.

23. The non-transitory computer-readable medium of claim 19, wherein the generating at least one respective maximum delay reverberator output includes:

weighting the input digital audio stream with a respective wet weight to produce a respective wet-weighted digital audio stream;

reverberating the respective wet-weighted digital audio stream with the at least one maximum delay reverberator to create at least one respective intervening output;

weighting the input digital audio stream with a respective dry weight to produce a respective dry-weighted digital audio stream; and producing the at least one respective maximum delay reverberator output by combining the at least one respective intervening output with the respective dry-weighted digital audio stream.

24. The non-transitory computer-readable medium of claim 23, wherein a ratio of the respective dry weight to the respective wet weight is in an inclusive range between one-to-one and twenty-to-one.

25. The non-transitory computer-readable medium of claim 19, wherein the generating at least one respective maximum delay reverberator output includes delaying the input digital audio stream by a maximum delay in an inclusive range between one sample cycle of the input digital audio stream to thirty sample cycles of the input digital audio stream.

26. The non-transitory computer-readable medium of claim 19, wherein the processor-executable instructions further include instructions configured to cause the processor to at least one of:

initiate attenuating, prior to the combining, the at least one respective intermediate delay reverberator output; or initiate attenuating, prior to the combining, the at least one respective maximum delay reverberator output.

27. An apparatus configured to enhance a signal-to-noise ratio, comprising:

means for generating a noise-cancelled digital audio stream from an input digital audio stream, wherein the means for generating the noise-cancelled digital audio stream include:

means for identifying a noise portion of the input digital audio stream;

means for inverting the identified noise portion; and means for adding the inverted identified noise portion to the input digital audio stream;

means for generating at least one respective intermediate delay output from the input digital audio stream;

means for generating at least one respective maximum delay output from the input digital audio stream; and means for combining the noise-cancelled digital audio stream, the at least one respective intermediate delay output, and the at least one respective maximum delay output to form an output digital audio stream having the enhanced signal-to-noise ratio.

28. The apparatus of claim 27, further comprising means for normalizing an intensity of the output digital audio stream to substantially an intensity of the input digital audio stream by weighting at least one of the noise-cancelled digital audio stream, the at least one respective intermediate delay output, or the at least one respective maximum delay output.

29. The apparatus of claim 27, wherein the means for generating at least one respective maximum delay output includes means for delaying the input digital audio stream by a maximum delay in an inclusive range between one sample cycle of the input digital audio stream to thirty sample cycles of the input digital audio stream.

30. The apparatus of claim 27, wherein the apparatus includes a hearing aid, an x-ray machine, a wireless router, a cell site device, a satellite, a space-based telescope, a missile guidance system, a sonar system, a cellular phone, a personal computer, a mixing board, a sound system, an amplifier, a car, a home appliance, a night-vision goggle, an augmented reality device, a virtual reality device, a laser-based eye surgery device, a radio device, a quantum computing device, a camera, a television, a radar device, or a drone aircraft, of which the means for generating at least one respective intermediate delay output is a constituent part.

* * * * *